United States Patent [19]

Farin et al.

[11] Patent Number: 4,860,745

[45] Date of Patent: Aug. 29, 1989

[54] HIGH FREQUENCY ELECTROSURGICAL APPARATUS FOR THERMAL COAGULATION OF BIOLOGIC TISSUES

[75] Inventors: Gunter Farin, Tubingen-Hirschau; Reiner Haag, Rietheim; Peter Putz, Tubingen, all of Fed. Rep. of Germany

[73] Assignee: Erbe Elektromedizin GmbH, Tubingen, Fed. Rep. of Germany

[21] Appl. No.: 74,553

[22] Filed: Jul. 15, 1987

[30] Foreign Application Priority Data

Jul. 17, 1986 [EP] European Pat. Off. ...... 86 109 794.7

[51] Int. Cl.[4] ............................................. A61B 17/39
[52] U.S. Cl. ................................................ 128/303.17
[58] Field of Search ..................... 128/303.13, 303.17, 128/303.18

[56] References Cited

U.S. PATENT DOCUMENTS

| | | | |
|---|---|---|---|
| 4,057,063 | 11/1977 | Gieles et al. | 128/303.17 |
| 4,114,623 | 9/1978 | Meinke | 128/303.17 |
| 4,188,927 | 2/1980 | Harris | 128/303.17 X |
| 4,271,837 | 6/1981 | Schuler | 128/303.14 |
| 4,321,926 | 3/1982 | Roge | 128/303.18 |
| 4,474,179 | 10/1984 | Koch | 128/303.17 |

FOREIGN PATENT DOCUMENTS

| | | | |
|---|---|---|---|
| 2540968 | 3/1977 | Fed. Rep. of Germany | 128/303.17 |
| 3420339 | 1/1985 | Fed. Rep. of Germany | 128/303.13 |
| 1347865 | 11/1963 | France . | |
| 2474307 | 7/1981 | France . | |
| 855459 | 11/1960 | United Kingdom | 128/303.17 |

Primary Examiner—Lee S. Cohen
Attorney, Agent, or Firm—Frishauf, Holtz, Goodman & Woodward

[57] ABSTRACT

A high frequency surgical apparatus for the thermal coagulation of biologic tissues is described, in which for monitoring the fluctuations in amplitude of the high frequency current during each coagulation process a current monitor (25) is provided, which by means of a current-to-voltage coverter generates an electrical voltage proportional to the amplitude fluctuations of the high frequency current, from which voltage, by means of a first detector, a first direct voltage proportional to the amplitude fluctuations is formed and, by means of a second detector acting as a peak value detector, a second direct voltage is formed that rises in proportion to the amplitude of the high frequency current. The first direct voltage ($U_a$) and the second direct voltage ($kU_b$), which is divided downward by an adjustable factor by means of a voltage divider, are supplied to a voltage comparator, the output signal of which sets a bistable circuit as soon as the first direct voltage ($U_a$) becomes lower than the downwardly divided second direct voltage ($kU_b$). The output signal of the bistable circuit switches the high frequency current off until the high frequency current is switched back on again by actuation of a manual switch and/or by means of an automatic switch. Instead of or in addition to this current monitor (25), and electric arc monitor (26) for monitoring the generation of anharmonic frequencies of the base frequency of the frequency generator can be connected to the output of the surgical apparatus, the arc monitor including a filter which passes at least one of the anharmonic frequencies, generated by the electric arc, of the base frequency of the high frequency generator. The output signal of the filter is supplied to a voltage comparator, the output signal of which resets a bistable circuit such that its output signal switches off the high frequency current.

10 Claims, 14 Drawing Sheets

HIGH FREQUENCY ELECTROSURGICAL APPARATUS FOR THERMAL COAGULATION OF BIOLOGIC TISSUES

BACKGROUND OF THE INVENTION

This invention concerns a high frequency electrosurgical apparatus for coagulation of biological tissue of a patient, of the kind comprising a high frequency generator of electrical alternating current and voltage, equipped with switching arrangements for manual or automatic activation of the high frequency current and for automatic termination of the coagulation operation as soon as it has reached a certain stage.

Thermal coagulation of biologic tissues, hereinafter called coagulation, by means of high frequency alternating electrical current and voltage, hereinafter simply called high frequency current, has been used for over 50 years in human and veterinary medicine for devitalizing diseased tissues and for closing perforated blood vessels. To this end, the high frequency current is conducted through the tissue to be coagulated so that the heating of the tissue experiencing the current takes place endogenically. The heating of the tissue is dependent on various parameters, such as the amount of tissue to be coagulated, the intensity of the high frequency current, the specific electrical resistance of the tissue to be coagulated, the duration of flow of the high frequency current, the specific heat capacity of the tissue to be coagulated, the shape and size of the coagulation electrodes, the heat dissipation through the coagulation electrodes, and also on whether the coagulation is performed in a monopolar or bipolar manner.

Since these parameters vary to a more or less great degree both during a coagulation process and from one coagulation process to another, the replicability of a desired quality of coagulation is very difficult to obtain and requires great attention and skill on the part of the operator.

In the various fields of surgery, various coagulation techniques have been developed, requiring satisfactory properties in the equipment used for the coagulation. As a rule, in nearly all surgical fields, conventional high frequency surgical devices are used for the different coagulations that even today have only adjusting devices for the intensity of the high frequency current and switches for switching the high frequency current on and off. And when these conventional high frequency surgical devices are used, the operator adjusts the intensity of the high frequency current at the adjusting device in accordance with his experience and allows the high frequency current to flow through the tissue to be coagulated until such time as he has the impression that the coagulation is completed.

Since as a rule the coagulation processes elapse within only 0.5 to 5 seconds, and changes in the coagulating tissue can become perceptible to the operator only within a fraction of these relatively short coagulation times, it is in practical terms almost impossible to terminate the coagulation process manually at precisely the time at which the coagulation is optimal. If the operator sets the intensity of the high frequency current too low and/or switches off the high frequency current too early, then the coagulation temperature is not attained and coagulation is inadequate. If the operator sets the intensity of the high frequency current too high and/or switches the high frequency current off too late, then the temperature of the coagulate rapidly increases beyond the required coagulation temperature, to above 100° C., which can very rapidly cause endogenic vapor formation within the coagulate and hence entail the explosive collapse of the coagulate, so that the intended goal of coagulation, especially when the coagulation is used for closing perforated blood vessels, is not attained.

Optimal coagulations are particularly difficulty to attain if the operator is not able to observe to coagulation process, for example if the coagulation has to be performed by means of invasive coagulation electrodes, such as in stereotactic operations in the neurosurgical field, or in tranvenous ablation of an accessory pathway in therapy-resistant supraventricular reentry tachycardias, as well as in transabdominal tubal ligation.

Attempts have been made for many years to devise an apparatus which automatically terminates the coagulation process as soon as the coagulation has attained a defined stage.

From German Patent Disclosure Document DE-OS No. 31 20 102, an apparatus for high frequency coagulation of albumen for surgical purposes, which is intended to shut off the high frequency current at the instant when the impedance or electrical resistance of the coagulate progresses through a certain change during the coagulation process.

It has been known for many years that the specific electrical conductance of electrolyte-containing biologic tissues largely increases in proportion to the temperature of this tissue. However, as soon as the temperature at which coagulatable components of the tissue coagulate is reached, which is the case between approximately 50° C. and 80° C., the increase in the electrical conductance becomes progressively less as a function of the temperature. Above 80° C. and in particular in the vicinity of the boiling point of intracellular and extracellular fluids, the electrical conductivity decreases rapidly. The cause of this rapid decrease in electrical conductivity above 80° C. is suspected to be both endogenous vapor formation and the dessication or drying up of the coagulate.

In the apparatus for high frequency coagulation of albumen, in particular for surgical purposes, described in German Patent Disclosure Document DE-OS No. 31 20 102, the albumen impedance is determined continuously while high frequency power is being supplied and the differential quotient for the impedance curve is formed as a function of time. The values of the differential quotient serve first to set the initial power, and second to determine the optimal instant for shutoff of the high frequency power. For both situations, preadjustments are provided that make for a flexible and simply adaptable apparatus. The apparatus is intended preferably for bipolar coagulation instruments, but use with unipolar instruments is also possible.

The use of this apparatus is problematical because the changes in impedance of the coagulating tissue are not continuous, as a result of fluctuations in the contact pressure between the coagulation electrode and the tissue caused by trembling of the hand of the operator and by shrinkage of the coagulating tissue, and instead more or less fluctuate about a mean trend. As a result, there are many undefined zero positions of the differential quotient. Furthermore, the differential quotient during slowly elapsing coagulations, because of the slow changes in the albumen impedance, is so small that a defined shutoff time does not exist.

It is an object of the invention to provide an apparatus for the thermal coagulation of biologic tissue by high frequency electric current in which the coagulation operation is controlled in such a way that better operation results are attainable while at the same time the surgeon is relieved of the responsibility of manually measuring out short intervals of time, and instead the coagulation operation can be automatically terminated at a precisely defined condition of coagulation.

THE INVENTION

Briefly, in a first embodiment, a current monitor is provided in the apparatus, including a device for producing a voltage proportional to current, for providing an electrical voltage proportional to the amplitude fluctuations of the high frequency current and a first detector produces a first DC voltage proportional to these amplitude fluctuations, while a second detector operating as a peak detector produces a second DC voltage which rises proportionally with rising amplitude of the high frequency current but does not appreciably decline from the peak values at which the fluctuations top out. Then the first DC voltage is compared with an adjustable fraction of the second DC voltage and is connected so as to set a bistable circuit to produce an output that turns off the high frequency current when the first DC voltage becomes smaller than the aforesaid fraction of the second DC voltage. The high frequency current remains cut off until either a manual switching operation, an automatic switching device or both being operated, restores the activation of the high frequency. In a second embodiment, the high frequency current is filtered to monitor the formation of an electric arc between the coagulation electrode of the apparatus and the tissue of the patient by filtering out frequencies that are not harmonically related to the fundamental frequency of the high frequency generator, such as the second harmonic of the power frequency. At the filter output for detecting formation of an electric arc, the fundamental frequency and the harmonics of the high frequency generator are damped. The output signal of the filter is compared as a reference value signal to produce an output for resetting a bistable circuit in such a way that its output signal switches off the high frequency current until, as in the case of the first embodiment, the high frequency current is manually or automatically switched on or is switched on as a result of the operation of both a manual and automatic switch.

The features of the first and second embodiments can be combined into a single apparatus so that the desired state of coagulation for shutting off the high frequency generator can be determined either by the comparison of current amplitude fluctuations with a reduced scale of peak detection of those fluctuations or else by the intensity of electrical arc formation at the surface of the coagulating tissue. These criteria, according to the invention, for determining the state of coagulation in which the high frequency generator of an electrosurgical coagulation device should be shut off have been found to be unambiguously applicable and suitable for reliably shutting off the generator and reducing the risk of excessive or inadequate coagulation.

THE DRAWINGS

FIG. 5 is a block circuit diagram of a further embodiment of the apparatus according to the invention shown in FIG. 4a;

DESCRIPTION OF THE ILLUSTRATED EMBODIMENTS

Figure 1:
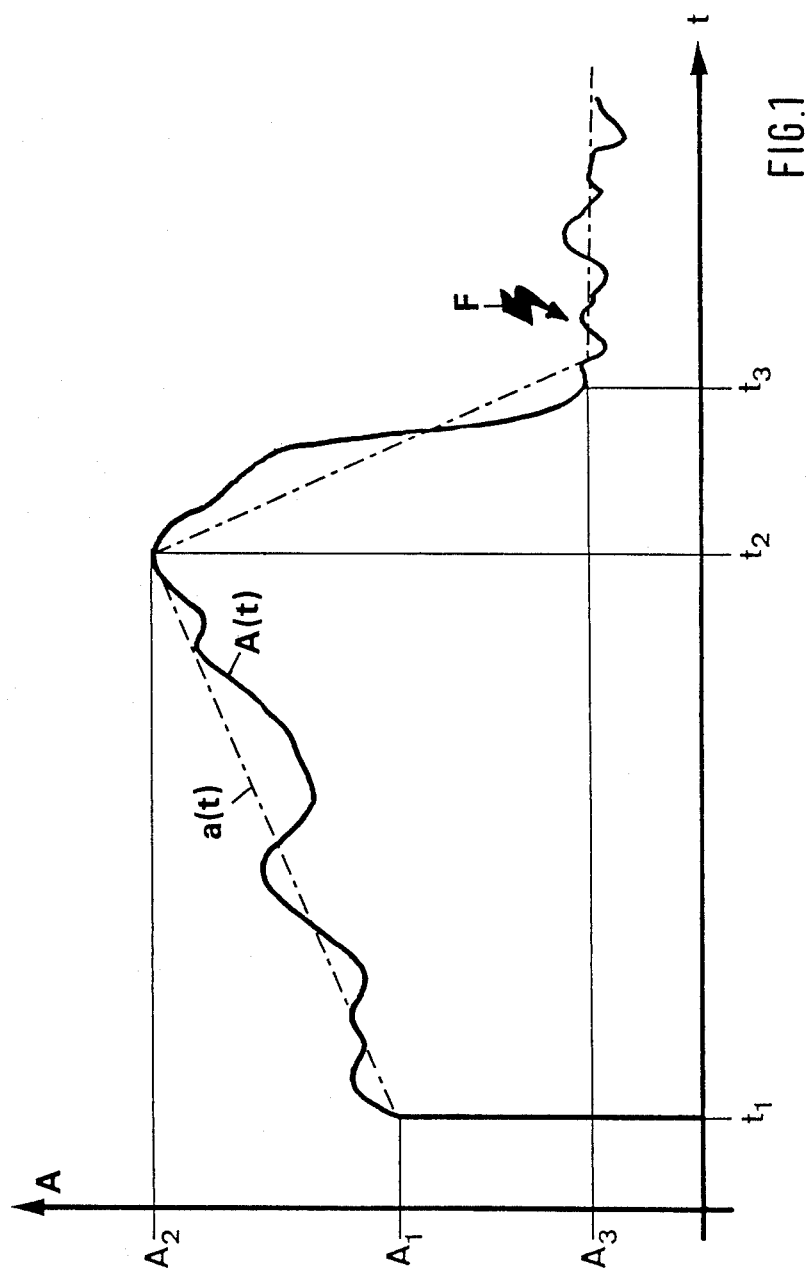
FIG. 1 shows a typical course of the amplitude changes of the high frequency current during a coagulation process.

In FIG. 1, a typical course of the amplitude changes $A(t)$ of the high frequency current during a coagulation process is shown, from which course a defined signal for shutoff of the high frequency current is to be derived.

At time $t_1$ at which the high frequency current begins to flow through the biological tissues to be coagulated, the amplitude A of the high frequency current attains the amplitude $A_1$, as a function of the aforementioned parameters. As a consequence of heating of the biologic tissue, the electrical conductivity of which is due to the electrolyte contained in it, the electrical conductivity and hence the amplitude A of the high frequency current increases. As soon as the temperature of the biologic tissue has risen to approximately 70° C., the coagulatable components of the biologic tissue coagulate, causing its electrical conductivity to decrease, so that the amplitude A of the high frequency current drops more or less rapidly from the maximum amplitude $A_2$ attained at time $t_2$. The drop in amplitude of the high frequency current as a function of the temperature of the coagulate is accelerated by the vaporization of the tissue fluids, as a result of which the coagulate dries out. As soon as the drying out of the coagulate, also known as dessication, has reached a certain stage at which the amplitude A of the high frequency current has dropped to a negligible level $A_3$, the coagulation process comes to a stop.

A decisive factor in discovering a suitable solution for the automatic shutoff of the high frequency current at a defined instant of the coagulation process on the basis of the changes in amplitude of the high frequency current or the changes in the impedance of the coagulate is the observation of the discontinuous changes in the amplitude $A(t)$ of the high frequency current during the coagulation process. As already mentioned above in the discussion of the prior art, the amplitude $A(t)$ of the high frequency current during each coagulation process fluctuates to a variably great extent about the mean trend $a(t)$ of the amplitude of the high frequency current. These more or less pronounced fluctuations in the amplitude of the high frequency current during each coagulation process result especially from the nonuniform contact pressure of the coagulation electrode against the tissue to be coagulated, which is due to uncontrolled movements of the hand of the operator and/or to the shrinkage of the coagulating and dessicating tissue.

Known apparatuses for thermal coagulation of biologic tissues which attempt to derive a defined shutoff criterion from the changes in amplitude of the high frequency current or from the changes in impedance of the coagulate ignore the above-described discontinuities in the changes in amplitude $A(t)$ and are based on the change $a(t)$, which in practice exists only seldom, that represents the theoretically averaged trend of the usually discontinuous change $A(t)$.

As can be seen from the examples shown in FIG. 1 of a realistic course of the amplitude changes $A(t)$ over the time t, the differential quotient $dA(t)/dt$ does not provide an unambiguous criterion for shutting off the high frequency current. An apparatus that is suitable for the automatic shutoff of the high frequency current and thus the termination of the coagulation process will now be described, referring to FIGS. 2 and 3.

A further criterion that can be utilized at the end of a coagulation process for automatic shutoff of the high frequency current is the igniting of electrical arcs or sparks between the coagulation electrode and the coagulate. The generation of electrical arcs or sparks, hereinafter simply called arcs, at the end of coagulation processes has already been known for many years. However, until now there was a lack of suitable methods and means for suitably electronically monitoring the ignition and presence of arcs between the coagulation electrode and the coagulate and for deriving suitable shutoff signals from that. An arc monitor suitable for the automatic shutoff of the high frequency current is described in conjunction with FIGS. 12 and 13.

Electric arcs as a rule are produced from time $t_3$ on. However, they may also occur even before time $t_3$, that is, once the amplitude $A_1$ of the high frequency current at time $t_1$ is already so high that in the boundary region between the coagulation electrode and the tissue such a high electrical field intensity is present that electric arcs can ignite. This occurs, for instance, if the high frequency generator is switched on before the coagulation electrode has electrically conductively touched the tissue and the coagulation electrode is touching the tissue at time $t_1$ with the high frequency generator already switched on. Accordingly, an apparatus is needed which prevents the switching on of the high frequency generator whenever the coagulation electrode does not have an electrically conductive contact with the tissue. An apparatus suitable for this will be described hereinafter, in conjunction with FIG. 10.

The ignition of electric arcs prior to $t_3$ or even prior to $t_2$ is also possible whenever the initial amplitude $A_1$ of the high frequency current at the switching on time $t_1$ is still too high, even though the coagulation electrode is touching the tissue in an electrically conductive manner before the high frequency generator has been switched on. Accordingly, an apparatus is needed that controls the amplitude of the high frequency current such that the initial amplitude $A_1$ at the switching on time $t_1$ is not too high, and in the time interval from $t_1$ to $t_2$ or $t_3$ is suitably controlled. An apparatus suitable for this will be described hereinafter, in conjunction with FIG. 6.

Figure 2:
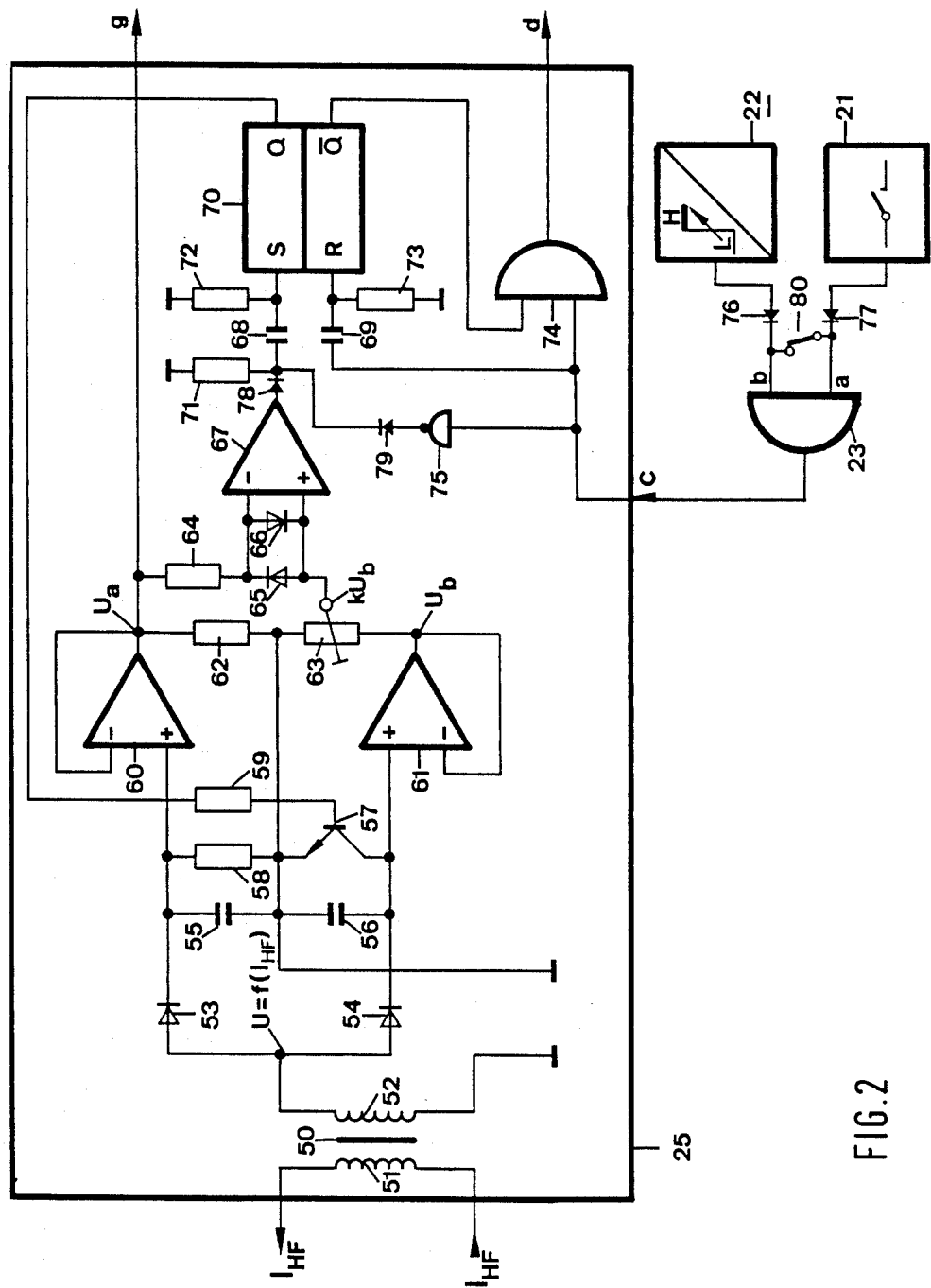
FIG. 2 shows a current monitor by means of which the course of the changes in amplitude of the high frequency current during a coagulation process is monitored and a defined shutoff instant is ascertained.

In FIG. 2, the details relative to the invention of an exemplary embodiment of a current monitor 25 are shown. By means of a current-to-voltage converter 50-52, a voltage $U=f(I_{HF})$ is formed that is proportional to the high frequency current $I_{HF}$, and this voltage is delivered to two detectors functioning differently from one another.

A first detector, comprising a diode 53, a capacitor 55, a resistor 58, a voltage follower 60 and a resistor 62 should be dimensioned such that its output voltage $U_a$ as rapidly as possible follows up the amplitude fluctuations of the voltage $U=f(I_{HF})$. The time constant of the parallel circuit of the capacitor 55 and resistor 58 should preferably be dimensioned such that on the one hand the basic frequency of the high frequency current, for example 500 kHz, is suppressed at the input of the voltage follower 60, but on the other hand amplitude fluctuations of the high frequency current are present in a form that is as undamped as possible in the output signal $U_a$ of the voltage follower 60. In dimensioning this time constant, the modulation of the high frequency current $I_{HF}$ caused by power line hum must also be taken into consideration. Here, the term power line hum means the fluctuations in amplitude of the high frequency current $I_{HF}$ caused by absent or incomplete smoothing (filtering) of the operating voltage of the high frequency generator, so that the amplitude of the high frequency current $I_{HF}$ is modulated to a variably great extent, with twice the power frequency. If too much power line hum is contained in the high frequency current $I_{HF}$, then the time constant of the elements 55 and 58 must be dimensioned such that this power line hum is adequately supressed at the input of the voltage follower 60, but that worsens the frequency response of the first detector. It is accordingly recommended that the supply voltage of the high frequency generator be filtered as well as possible.

A second detector, comprising a diode 54, a capacitor 56, a voltage follower 61 and a voltage divider 63, should be dimensioned such that it acts as a peak value detector, so that the output voltage $U_b$ rises in proportion to the peak values of the voltage $U=f(I_{HF})$.

The voltage $U_a$ and the voltage $kU_b$, which is divided downward by an adjustable factor k, which must be less than 1, are simultaneously carried to a voltage comparator 67. In a known manner the two diodes 65 and 66 secure the input of the voltage comparator against overly high voltage differences.

The mode of operation of the two detectors described above and of the voltage comparator in the current monitor 25 will now be described, referring to the diagram of FIG. 3. The curve $U_a(t)$ represents the output voltage $U_a$ over the time t during one coagulation process. In the same diagram, two different curves are shown, for example, which represent the voltage $kU_b(t)$ that is divided downward by an adjustable factor k. For one curve, k was set to be equal to 0.8, and for the other curve k was set to be equal to 0.5. Depending on the setting of the factor k, the curve $kU_b(t)$ intersects the curve $U_a(t)$ earlier or later within the time interval $t_2$-$t_3$. The voltage comparator 67, at time $t_k$, furnishes a positive voltage at its output as soon as the voltage $U_a(t)$ becomes smaller than $kU_b(t)$, which a bistable circuit 70, for example an RS flip-flop, sets dynamically via the capacitor 68 in such a way that its output signal $\overline{Q}$ becomes 0. At the same time, the capacitor 56 of the peak value detector is discharged by the transistor 57, for which purpose the output signal Q=1 of the RS flip-flop is used.

The output signal d of the current monitor 25 switches the high frequency current $I_{HF}$ on or off, this output signal d being dependent on the AND condition 74 of the signals $\overline{Q}$ of the RS flip-flop 70 and of the signal c from the switches 21 and/or 22.

After every automatic shutoff of a coagulation process, the bistable circuit 70 remains in the state Q=1 and $\overline{Q}$=0, until the signal c jumps from logical 0 to 1 by being switched on manually 21 or automatically 22 and resets it via the capacitor 69.

If the signal c is switched from logical 1 to 0 during the coagulation process as a result of premature shutoff of the manual switch 21 and/or automatic switch 22, then the bistable circuit 70 is set by means of the signal $\bar{c}$ inverted in the inverter 75 such that Q=1 and the capacitor 56 is discharged via the transistor 57. The other elements of FIG. 2 are either known to one skilled in the art in terms of their function, or will be described hereinafter.

Instead of automatically deriving a defined shutoff time $t_k$ from the changes in amplitude of the high frequency current $I_{HF}$, this shutoff time can also be derived from the changes in amplitude of the high frequency voltage $U_{HF}$ at the output 11, 12 of the apparatus. To this end, the same current monitor 25 can be used, but the current-to-voltage converter 50–52 is omitted and instead a high frequency rectifier or demodulator, which rectifies or demodulates the high frequency voltage $U_{HF}$ and an inverter, which inverts the thus-obtained direct voltage, are necessary. The term inverter here refers to an apparatus which inverts a rising voltage level into a dropping voltage level and a dropping voltage level into a rising voltage level. The high frequency voltage $U_{HF}$ modulated and inverted in this manner can be supplied directly to the two detectors of the current monitor 25.

Furthermore, a defined shutoff time $t_k$ can be derived from the change in the electrical conductance value of the tissue between the monopolar coagulation electrode 15 and the neutral electrode 18, or between the two poles of a bipolar coagulation electrode 13. To this end, the conductance value is calculated electronically from the amplitudes of the voltage $U_{HF}$ and current $I_{HF}$, for example by means of known analog divider circuits. The output voltage of the electronic analog divider, which voltage is proportional to the conductance value, can be supplied like the voltage $U=f(I_{HF})$ to the two detectors of the current monitor 25.

Deriving the shutoff time $t_k$ from the changes in the electrical conductance of the tissues during the coagulation process is more expensive than deriving it from the changes in amplitude of the high frequency current $I_{HF}$ or the high frequency voltage $U_{HF}$, but it does have the advantage that fluctuations in amplitude caused by the high frequency generator, for example because of power line hum or fluctuations in the power system voltage, are automatically eliminated.

Instead of the current-to-voltage converter 50–52 shown in FIG. 2, other current-to-voltage converters are also usable for this purpose, such as photoelectric or thermoelectric current-to-voltage converters. Preferably, current-to-voltage converters of the kind that react fast enough, that have a potential separation with the maximum possible voltage stability between the input 51 and the output 52 and that have the lowest possible capacitive coupling between the input and the output will be used.

Referring to a block circuit diagram in FIG. 4, an exemplary ebodiment of an apparatus according to the invention for thermal coagulation of biologic tissues by means of high frequency current will now be described.

The high frequency generator that generates the high frequency current $I_{HF}$ for the coagulation process comprises a high frequency oscillator 1, an amplitude modulator 2, a power amplifier 3 and an output transformer 4.

The amplitude A of the high frequency current $I_{HF}$ is the product of the no load voltage $U_o$ of the high frequency generator and the sum of all the resistances in the current circuit. The no load voltage $U_o$ can be adjusted in a known manner at an adjusting device 9 and is realized by the amplitude modulator 2. The amplitude modulator 2 is for example a preamplifier, the amplification factor of which is adjustable at the adjusting device 9. Since the electrical resistance of the biologic tissue to coagulated, and in particular the quantity of resistance changes in the tissue to be coagulated, should be as great as possible during the coagulation processes in comparison with the sum of all the partial resistances determining the high frequency current $I_{HF}$, so that these changes in resistance will be recognized without difficulty by the current monitor 25, care should be taken that all the partial resistances, in particular the internal resistance of the high frequency generator, be as low as possible, for example 50 ohms for bipolar coagulation and 200 ohms for monopolar coagulation. After switching on the manual ON switch 21, the current monitor 25 is activated by the signal c, which for example comprises logical voltage levels (L=LOW, H=HIGH), and the current monitor simultaneously switches the high frequency oscillator on by means of the signal d via the line D.

Figure 4:
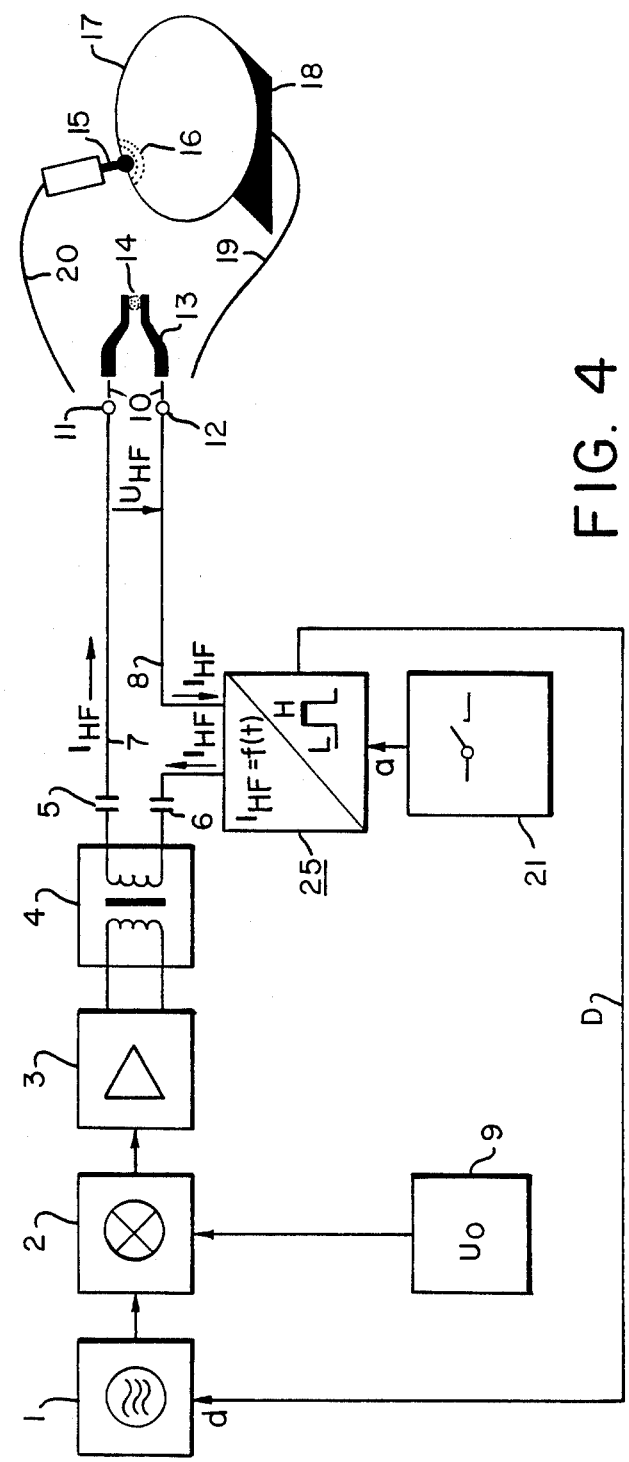
FIG. 4 is a block circuit diagram of an exemplary embodiment of the apparatus according to the invention for thermal coagulation of biologic tissues by means of high frequency current.

The function of the current monitor 25 shown in detail in FIG. 2 has already been described above, but with the distinction that in the exemplary embodiment of FIG. 4 only one manual switch 21 is used. Naturally, the exemplary embodiment shown in FIG. 4 can be equipped alternatively or additionally with an automatic switch 22. Automatic switchgear is known from German Examined Application No. 1 099 658, German Pat. No. 2 540 968 and German Patent Application No. 2 946 728.

Figure 3:
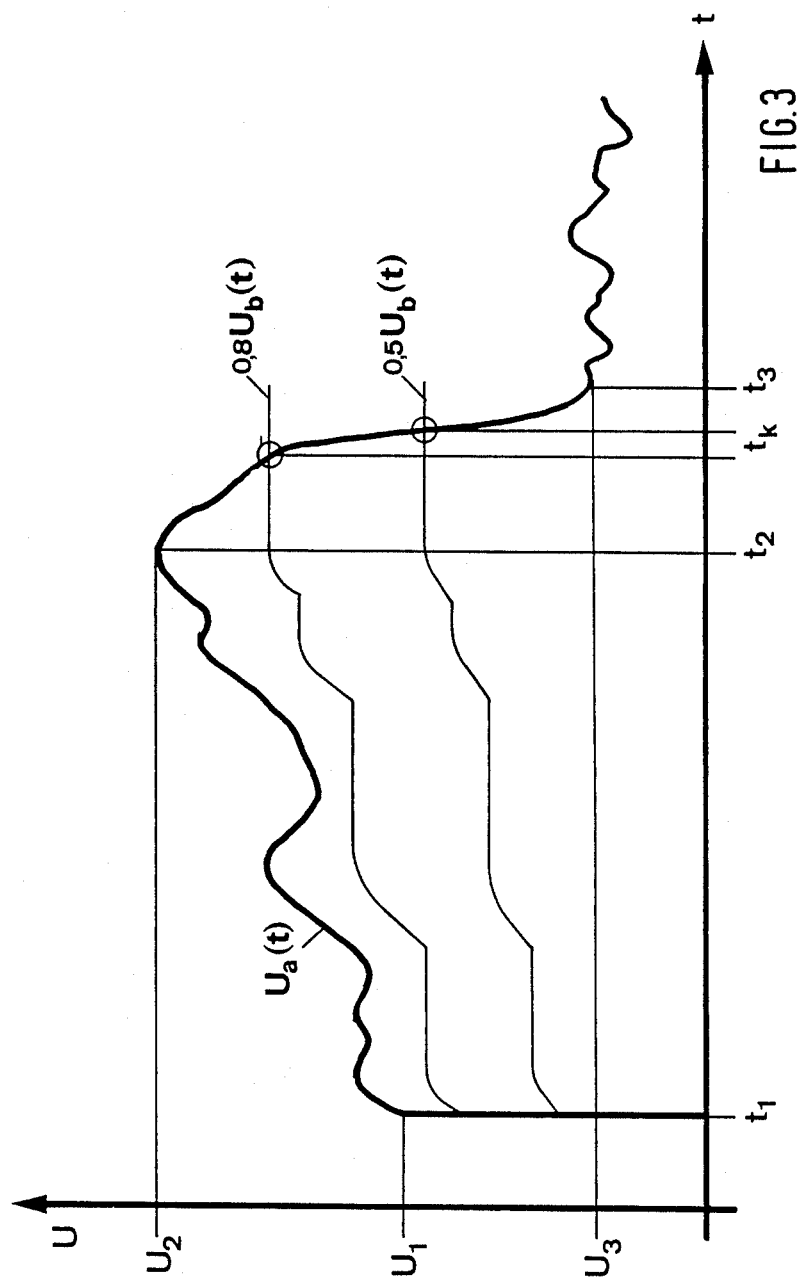
FIG. 3 is a diagram showing the course of the electrical voltages $U_a$ and $kU_b$ during a coagulation process.

As soon as the shutoff criterion described in conjunction with FIGS. 2 and 3 has been attained, the high frequency oscillator 1 is automatically shut off by the signal d via the line D, until such time as the switch 21 is actuated again.

Suitable further features of the exemplary embodiment described in conjunction with FIG. 4 for an apparatus for thermal coagulation of biologic tissues by means of high frequency current will now be described, referring to FIGS. 5–12.

Figure 5:
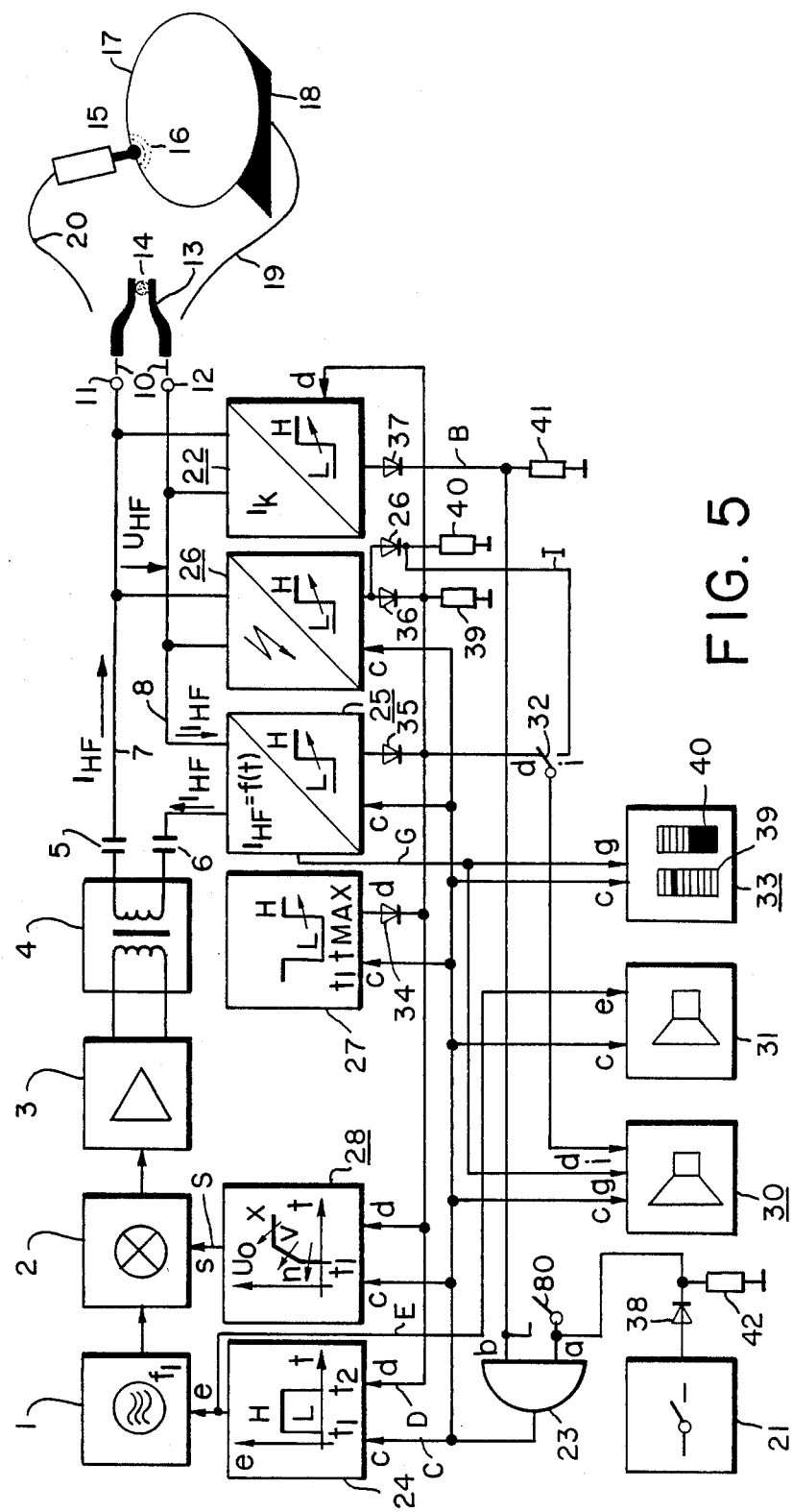

FIG. 5 is a block circuit diagram illustrating the cooperation of all the supplemental devices described in further detail hereinafter, which further improve the exemplary embodiment shown in FIG. 4 in terms of attaining the object of this invention.

Figure 4A:
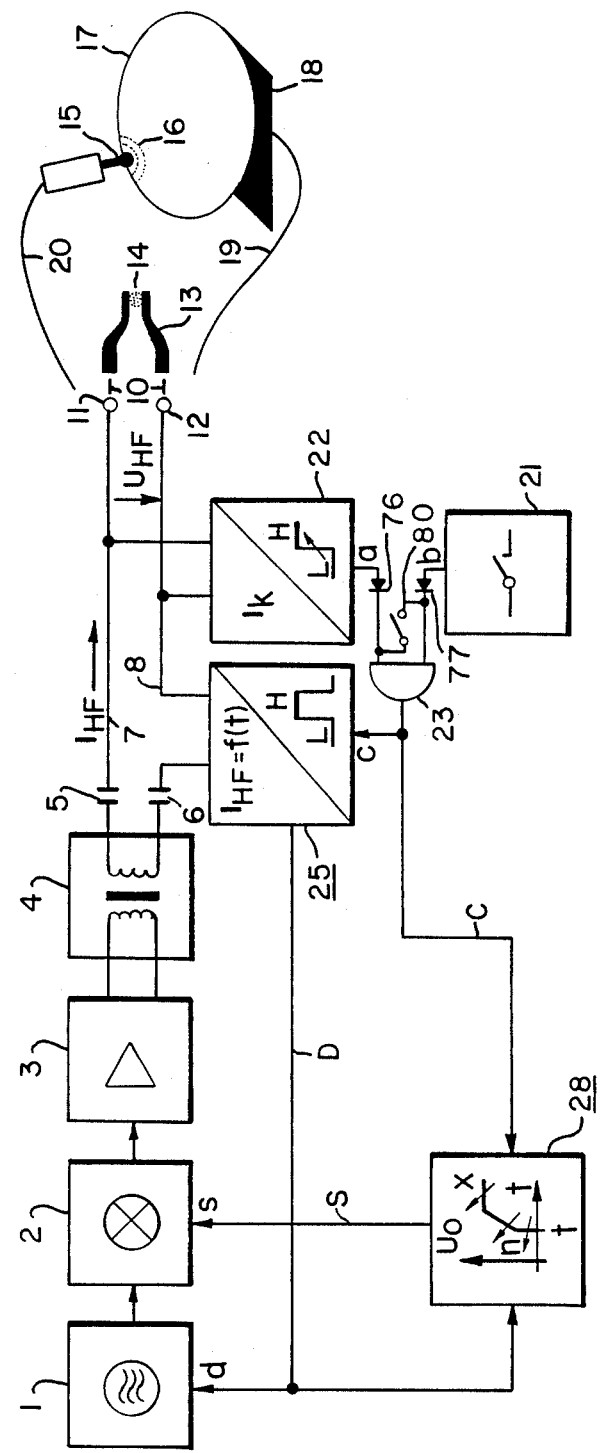
FIG. 4a is a block circuit diagram of a modification of FIG. 4.

A suitable improvement of the exemplary embodiment shown in FIG. 4 is shown in FIG. 4a. There, the control device 28, which controls the no load voltage $U_o$ of the high frequency generator, via the amplitude modulator 2, from an adjustable minimum level n at an adjustable speed v to an adjustable maximum level x. This control device is triggered by the switch on signal c via the line C in such a way that the adjustable minimum level n begins at time $t_1$ of the switching on of the oscillator 1. If the minimum level n is set to 0, then the voltage $U_o$ rises from 0, from time $t_1$ on. If the monopolar coagulation electrode 15 or the two poles of the bipolar coagulation electrode 13 is in electrically conductive contact with the tissue of the patient 17, then the current $I_{HF}$ also rises from 0. As a result, arbitrarily large or small coagulation electrodes can be used, without having to preset the high frequency power in accordance with the particular size of the coagulation electrode, as must be done in conventional high frequency surgery equipment. As soon as the shutoff criterion described in conjunction with FIGS. 2 and 3 has been attained, the coagulation process is terminated automatically. For large coagulations, in which only relatively large coagulation electrodes are used, it is advantageous to set a higher minimum level n. The control device 28 will be described hereinafter in further detail in conjunction with an exemplary embodiment.

In order to prevent the control device 28 from setting the no load voltage $U_o$ of the high frequency generator at a high level even before the coagulation electrode 15 or 13 electrically conductively touches the tissue to be coagulated, an automatic switch 22 is provided, which via an AND linkage 23 prevents the switching on of the oscillator 1 and the triggering of the control device 28 when the switch 80 is opened, until such time as either the monopolar coagulation electrode 15 simultaneously with the neutral electrode 18, or both poles of the bipolar coagulation electrode 13, simultaneously touch the tissue of the patient 17 in an electrically conductive manner. An exemplary embodiment of an automatic switch 22 suitable for this purpose will be described in further detail hereinafter, in conjunction with FIG. 10.

An automatic shutoff device, that is, the arc monitor 26 as shown in FIG. 5, is provided in order to increase the redundancy of the automatic shut-off function; this is important in view of the automatic control 28 of the no load voltage $U_o$ of the high frequency generator, because a failure of the shutoff function of the current monitor 25 would cause the optimal coagulation to be exceeded faster, especially when relatively small coagulation electrodes are used, than with conventional high frequency surgical equipment, which furnish a largely constant voltage $U_o$. In the event of failure of the shutoff function of the current monitor 25, the arc monitor 26 performs the shutoff at the moment when an electrical arc is produced between the coagulation electrode 15 or 13 and the tissue of the patient 17. An arc monitor 26 suitable for this purpose is described in further detail below, referring to FIGS. 12 and 13.

In the event that one or both of the above-described automatic criteria are absent, a compulsory shutoff is provided by means of an ON time limiter 27, which shuts off the high frequency generator after a predeterminable period $t_{max}$ has elapsed. This ON time limiter 27 is for example an electrical timer triggerable by a logic level c, which after an adjustable period $t_{max}$ has elapsed furnishes a signal d to the line D and as a result shuts off the high frequency generator and resets the devices 28, 22, 24, 30.

This ON tie limiter 27 must be equipped such that each trigger pulse c restarts the time interval $t_1$ up to $t_{max}$. An example of an ON time limiter suitable for this purpose is a post-triggerable time switch or a post-triggerable monostable circuit (literature: U. Tietze and Ch. Schenk, *Halbleiter-Schaltungstechnik* [Semiconductor Circuit Technology], fifth edition, pages 448 ff, published by Verlag Springer, Berlin, Heidelberg, New York, 1980).

The apparatus according to FIG. 5 can be selectively switched on manually by the manual switch 21 and/or automatically by the automatic switch 22, depending on whether the switch 80 is closed or open.

If the switch 80 is closed, then the apparatus can be switched on either manually or automatically. If the switch 80 is opened, then the apparatus can be switched on manually only whenever the conditions of the automatic switch 22 are fulfilled, that is, whenever the monopolar coagulation electrode 15 and the neutral electrode 18 or both poles of the bipolar coagulation electrode 13 simultaneously touch the tissue of the patient 17 in an electrically conductive manner. By means of this AND linkage of the two switches 21 and 22, the above-described condition for the automatic control device 28 is fulfilled, that is, that the voltage $U_o$ cannot be switched on until the coagulation electrodes electrically conductivity touch the tissue. Conversely, the automatic switch 22 can automatically switch on the apparatus only whenever the manual switch 21 is actuated. This AND linkage of the two switches 21 and 22 prevents an unintentional startup of the apparatus, for example if the bipolar coagulation electrode should touch the tissue of the patient unintentionally.

Figure 6:
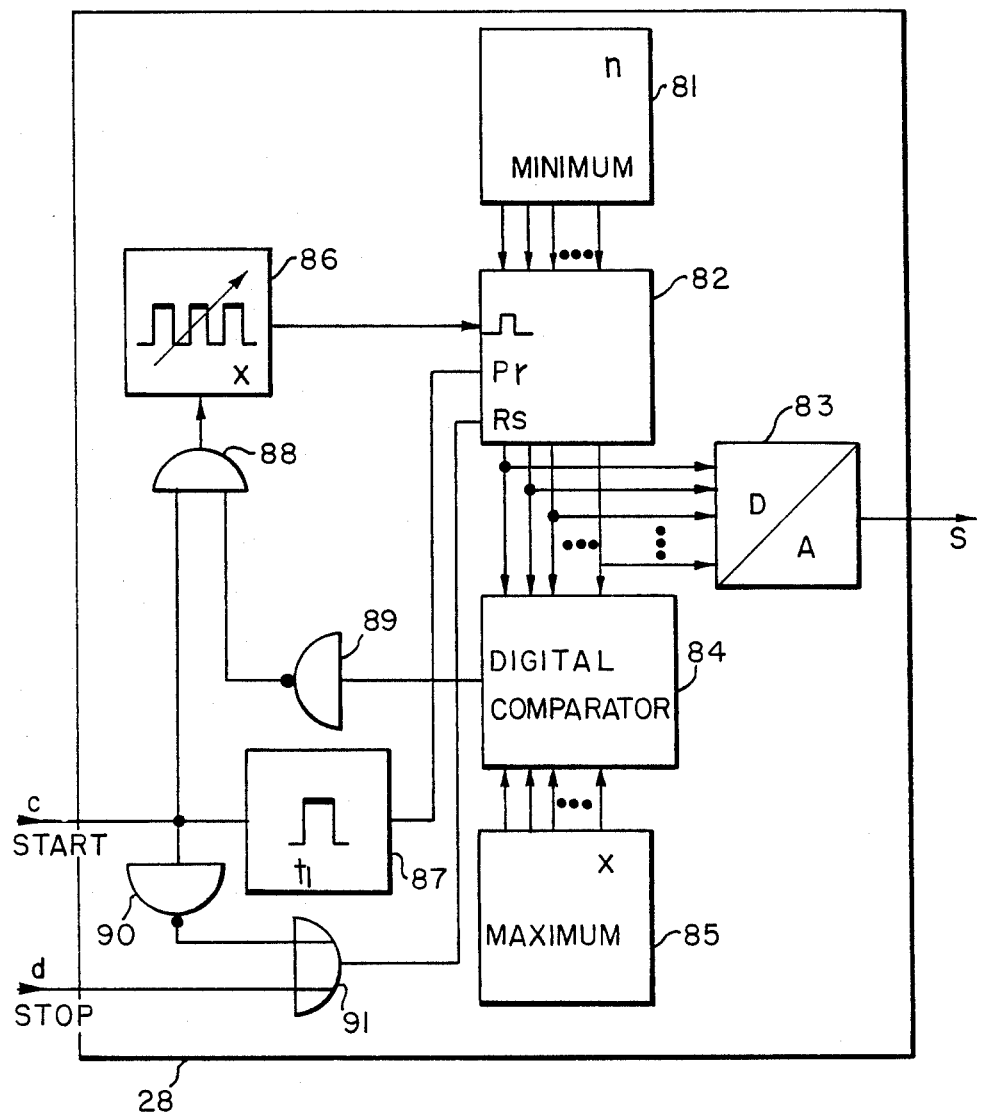
FIG. 6 is a block circuit diagram of an exemplary embodiment of the control of the no load voltage $U_o$ of the high frequency generator.

Turning to FIG. 6, an exemplary embodiment of a control device 28 for the automatic control of the no load voltage $U_o$ of the high frequency generator will now be described.

The automatic shutoff of the high frequency current $I_{HF}$, and hence the automatic termination of the coagulation process upon attainment of a defined stage of coagulation in which either the change in amplitude of the high frequency current $I_{HF}$ and/or the ignition of electrical arcs between the coagulation electrode and the tissue is used as a shutoff criterion, enables and demands automatic control of the coagulation power $P_{HF}=U^2HF/R$, where R stands for the real electrical load resistance at the output terminals 11 and 12, for example by means of controlling the no load voltage $U_o$ of the high frequency generator, so that the coagulation power $P_{HF}$ is a function of the no load voltage $U_o$ in accordance with the following equation:

$$P_{HF} = \left( \frac{U_o}{R_i + R_a} \right)^2 \cdot R_a$$

where $R_i$ is the internal resistance of the high frequency generator and $R_a$ is the real load resistance at the output terminals 11 and 12. If the coagulation power $P_{HF}$ rises more or less rapidly, for example from 0 on, beginning at a minimum level, then because of the automatic shutoff of the high frequency current $I_{HF}$, an optimal coagulation is always attained regardless of whether a very small or a large amount of tissue 14 is held between the poles of the bipolar coagulation electrode 13 and regardless of whether fine or coarse coagulation electrodes are used.

The no load voltage $U_o$ should be controlled automatically from a preadjustable minimum level $U_{min}$ at an adjustable speed v to a preadjustable maximum level $U_{max}$. The exemplary embodiment is realized using digital technology. The minimum level $U_{min}$ is adjusted at a digital preselection switch 81 and supplied in the form of a digital number n to a programmable counter 82. As soon as the signal e=start assumes a HIGH level, which corresponds to time $t_1$, the counter 82 is started via the preset input Pr by means of a short pulse that is formed by a monostable circuit 87, and the counter takes over the digital number n from the preselection switch 81. The signal e starts the pulse generator 86 via the AND element 88, the pulse frequency of the pulse generator being adjustable. Beginning at the number n preadjusted at the preselection switch 81, the counter 82 counts the pulses of the pulse generator 86 upward or downward, depending upon whether the digital number x, corresponding to the maximum level of the preselection switch 85, is defined as less than or greater than the digital number n corresponding to the minimum level.

The output of the counter 82 is carried to a digital comparator 84, which compares the digital number of the counter 82 with the digital number x of a preselection switch 85, at which the maximum level of the no load voltage $U_{max}$ is preadjusted. As soon as the digital number at the output of the counter 82 is equal to the digital number x of the preselection switch 85, the digital comparator 84 furnishes an output signal to the pulse generator 86, which shuts off the pulse generator. If a digital comparator is used, which from the time that there is equivalence of both digital numbers at its output furnishes a HIGH level, then this signal must be inverted, by means of an inverter element 89. A digital-/analog converter is connected to the output of the counter 82, and from the digital number it forms an analog voltage level s, which is delivered via the line S to the amplitude modulator 2. As soon as the signal e changes from a HIGH to a LOW level as a result of shutoff of the manual switch 21 or automatic switch 22, or the signal d changes from LOW to HIGH level, then the counter 82 is reset to 0 via its reset input Rs via the OR element 91. To this end, the signal e is inverted in the inverter element 90.

Figure 7:
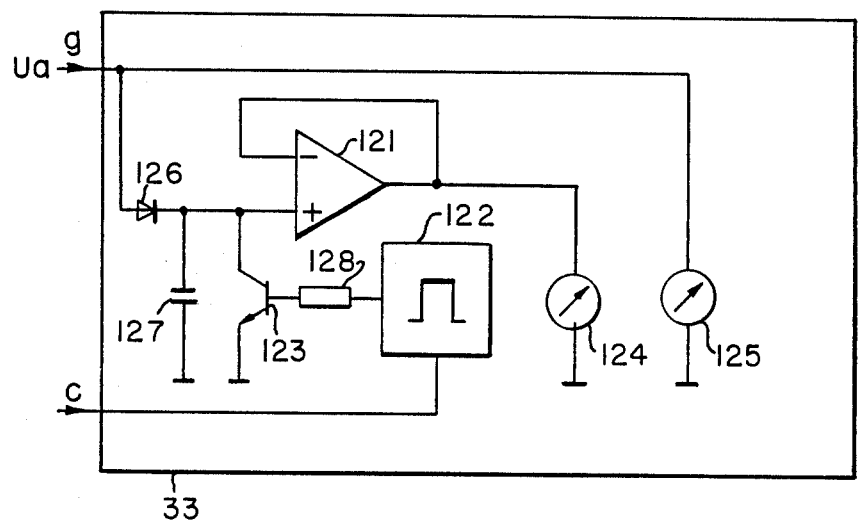
FIG. 7 shows an exemplary embodiment of the high frequency current indicator.

An exemplary embodiment of the high frequency current indicator 33 will be described in further detail below, referring to FIG. 7.

The high frequency current indicator 33 indicates to the operator, on an analog or digital display instrument 125, the instantaneous value of the current $I_{HF}$ at any time and, on another analog or digital display instrument 124, the peak value of the current $I_{HF}$ of each coagulation process. The corresponding measured values can be taken from the current monitor 25. The instantaneous value of the current $I_{HF}$, which is derived from the voltage $U_a$ of the current monitor 25, is displayed directly. The peak value of the current $I_{HF}$ of a coagulation process is stored by means of a peak value detector, comprising the diode 126, the capacitor 127 and the voltage follower 121, and displayed by the instrument 124 until such time as a new coagulation process is started by means of the signal c. The signal c triggers a monoflop 122, which furnishes a pulse to the base of the transistor 123 having a duration such that the capacitor 127 is sufficiently discharged.

The current indicator 33 informs the operator whether a current $I_{HF}$ is flowing, how much current $I_{HF}$ is flowing, and how high the current $I_{HF}$ had maximally risen during each coagulation process.

Figure 8:
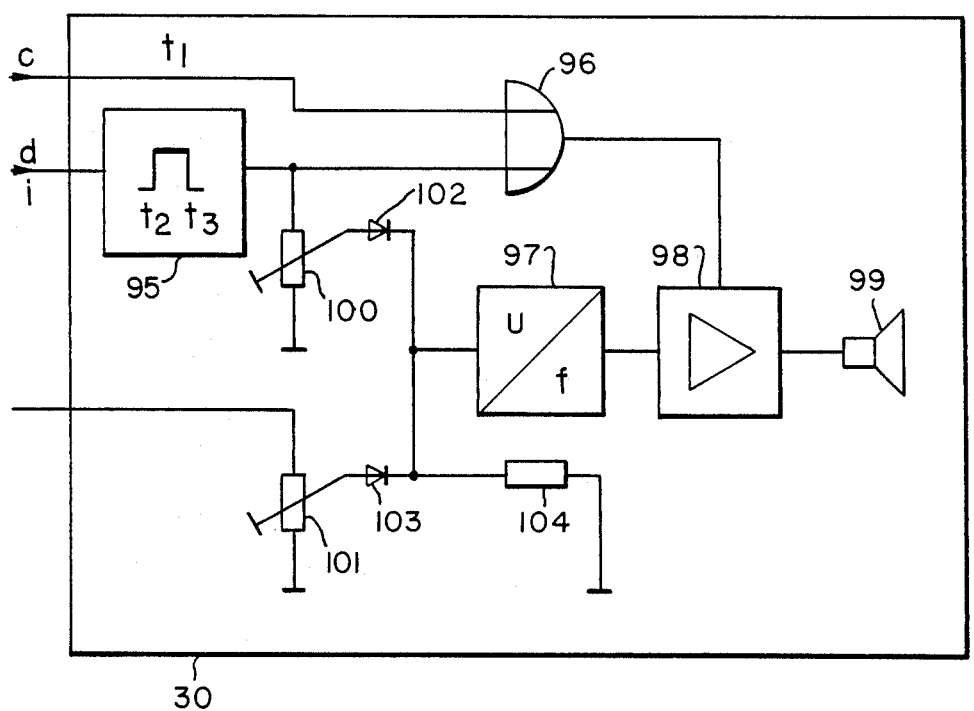
FIGS. 8 and 8a show an exemplary embodiment of an acoustical signal transducer which informs the operator about the coagulation process.
Figure 8A:
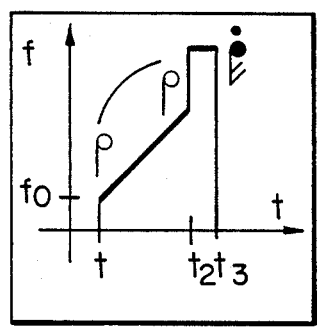

An exemplary embodiment of the acoustical signal transducer 30 will be described in further detail below, referring to FIGS. 8 and 8a.

This acoustical signal transducer 30 is intended to inform the operator acoustically about the coagulation process. This acoustical signal transducer 30 therefore generates variable tones which are associated with the particular coagulation process. At the instant the high frequency generator is switched on, this acoustical signal transducer 30 generates a tone having the frequency $f_o$, for example 130 Hz, when the current $I_{HF}$ is 0. The voltage/frequency converter 97 is embodied such that when $I_{HF}=g=0$, or in other words when no current $I_{HF}$ is flowing, it generates the basic frequency $f_o$. At the shutoff instant $t_2$, which is triggered by the shutoff signal d, the frequency of the acoustical signal jumps to a firmly set maximum frequency, for example 2000 Hz, which sounds in staccato fashion. The staccato tone $t_2$ through $t_3$ can be triggered either by the signal d or by the signal i, depending on how the switch 32 is switched. As a result, the operator has a simple opportunity of determining whether the automatic shutoff of the current $I_{HF}$ is taking place first by means of the arc monitor 26, or has already been done, as is generally to be expected, by means of the current monitor 25. The basic tone having the frequency $f_o$ informs the operator that the high frequency generator is switched on. From the tone frequency during the time interval $t_1$ through $t_2$, the operator recognizes the intensity or the changes in intensity of the current $I_{HF}$. From the high staccato tone, the operator recognizes the end of the coagulation process.

The tone frequency $f_{Ton}$ is generated in a voltage-to-frequency converter 97, also called VCO, amplified in an amplifier 98 and delivered to a loudspeaker 99. The amplifier 98 is activated via an OR element 96, either by means of the switchon signal c or for a short time interval from $t_2$ to $t_3$, staccato, by the signal d and either the basic tone $f_o$ preadjusted in the voltage-to-frequency converter 97, if it is activated by the signal c, or the staccato tone firmly set at the voltage divider 100 and having the high frequency of 2000 Hz for example, if it is activated by the signal d.

If a current $I_{HF}$ is flowing, then the frequency of the tone is modulated by means of the signal g, which represents a voltage proportional to the current $I_{HF}$, and for this purpose the voltage $U_a$ from the current monitor 25 can for instance be used, the modulation of the tone frequency being in proportion with this voltage. The tone frequency rises and falls with the intensity of the current $I_{HF}$.

Figure 9:
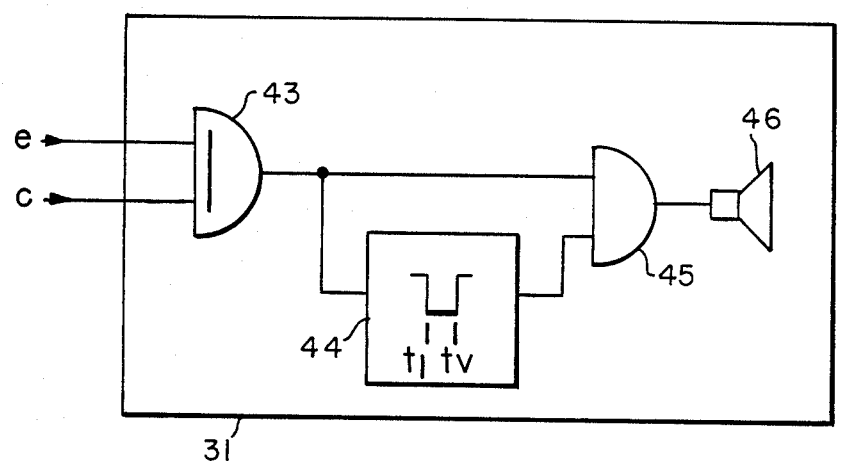
FIG. 9 shows an exemplary embodiment of a further acoustical signal transducer which informs the operator about apparatus malfunctions.

An exemplary embodiment of the acoustical signal transducer 31 will now be described in further detail, referring to FIG. 9. This acoustical signal transducer generates a warning signal if the high frequency oscillator 1 is unintentionally switched on by mistake, or if the high frequency oscillator is not activated even though the switches 21 and/or 22 have switched on. To this end, the signals c and e are compared in an exclusive-or element, where the following four possibilities can be provided.

| Case | c | e | Tone | Remarks |
|---|---|---|---|---|
| 1 | 0 | 0 | OFF | Proper function per set conditions. |
| 2 | 0 | 1 | ON | HF oscillator ON, even though no switch is switched on. FAULT condition! |
| 3 | 1 | 0 | ON | HF oscillator OFF, although switch 21 and/or 22 switched on. FAULT condition! |
| 4 | 1 | 1 | OFF | HF oscillator ON and switch 21 and/or 22 switched on. Proper function per set conditions. |

For case 3, a delay from $t_t$ to $t_y$ in the warning signal (tone) is present by means of a monostable circuit 44. This delay in the warning signal prevents the warning signal from briefly sounding each time there is a fault-free switch-on process as well resulting from unavoidable component-dictated or circuit-dictated delays between the signals c and e.

Instead of the signal e, this signal transducer can also be supplied with the signal g. As a result, case 3 in the above table in particular is more advantageously monitored, because by this means failures of the control device 28, the high frequency oscillator 1, the modulator 2, the power amplifier 3, the output transformer 4 and the capacitors 5 and 6 are monitored. Here, the delay from $t_1$ to $t_y$ of the monostable circuit 44 must be selected to be long enough that during the time until the signal g has attained a sufficient level for the input of the exclusive OR element, no warning signal will be generated.

In a further feature of this signal transducer, the delay from $t_1$ to $t_y$ could be linked in such a way with the control device 28 that this delay is automatically varied inversely proportionally to the minimum level n and to the rise speed v.

An exemplary embodiment of an automatic switch 22 will now be described in further detail, referring to FIG. 10.

Automatic switches or switch-on devices are already known from German Patent Disclosure Document DE-OS No. 28 23 291, German Patent Application No. 25 409 968 - c2, German Examined Patent Application No. 1 099 658 and U.S. Pat. No. 2,827,056. These known automatic switch-on devices are not, however, suitable directly for use in the apparatus according to the invention as shown in FIG. 5. When these known switch-on devices are combined with the automatic shutoff devices 25 or 26 according to the invention as shown in FIG. 5, these switch-on devices would switch the high frequency generator back on again immediately after the automatic shutoff if the coagulation electrode 13 or 15 remains in electrically conductive contact with the tissue of the patient 17, which is the rule in this kind of surgical technique.

Figure 10:
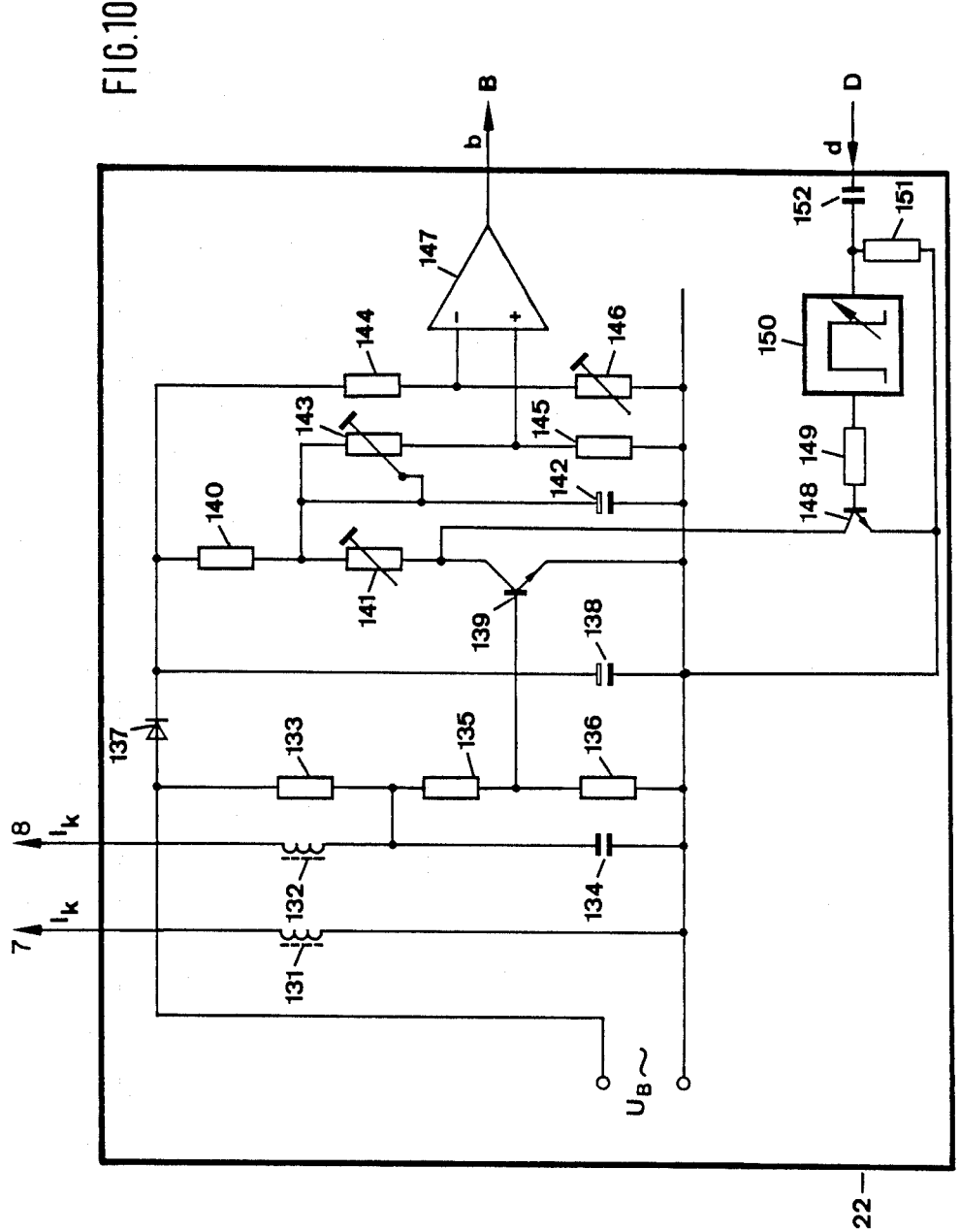
FIG. 10 shows an exemplary embodiment of an automatic switch.

The automatic switch 22 shown in FIG. 10 is advantageously improved in comparison with known switches in that a pause of adjustable duration following every automatic shutoff is introduced, during which pause the operator can lift the coagulation electrode away from the tissue without haste, before the automatic switch 22 switches the high frequency generator back on.

As a criterion of automatic ON/OFF switching of the high frequency generator, a control current $I_k$ is utilized, which via the monopolar electrode 15 or bipolar electrode 13 flows through the tissue of the patient 17 whenever the monopolar coagulation electrode 15 and the neutral electrode 18, or both poles of the bipolar electrode 13, simultaneously electrically conductively touch the tissue of the patient 17. To this end, the automatic switch 22 includes a voltage source $U_B$, which preferably is a source of alternating voltage, and a current indicator, which ascertains whether or not a control current $I_k$ is flowing. As the voltage source of the voltage $U_B$, an alternating voltage of 50 Hz from a mains transformer can be used. As the current indicator, a voltage comparator 147 can for instance be used, which monitors the voltage drop at a resistor in the control current circuit, in which case the alternating voltage must previously be rectified. To prevent the immediate switching on of the high frequency generator whenever the control current $I_k$ flows, a post-triggerable switch-on delay is provided, which is realized by means of the elements 131–143.

For instance if the bipolar coagulation electrode 13 simultaneously touches the tissue of the patient 17 with both poles in an electrically conductive manner, then the base voltage of the transistor 139 becomes so low that this transistor blocks. As a result, the capacitor 142 can be charged more or less rapidly via the resistors 140 and 143, depending on how the resistor 143 is adjusted. If the voltage at the positive input of the voltage comparator 147 exceeds the voltage set at the voltage divider 144, 146, then the output b of the voltage comparator 147 becomes positive and switches the high frequency generator on. The switch-on delay, that is, the time between the electrically conductive touching of the tissue with both poles of the bipolar coagulation electrode 13 until the instant at which the output signal b of the voltage comparator 147 switches over from negative to positive, can be adjusted either by varying the charge time constant by means of the trimming resistor 143 and/or by means of varying the voltage at the negative input of the voltage comparator 147 by means of the trimming resistor 146. If the electrically conductive contact of the bipolar coagulation electrode 13 with the tissue is interrupted, then the transistor 139 becomes conductive immediately and discharges the capcitor 142 very rapidly via the trimming resistor 141. A second transistor 148 is connected in parallel according to the invention with the transistor 139 of the switch, which up to this point is already known. By means of the shutoff signal d via the line D, by means of a monostable circuit 150 having an adjustable pulse duration, this second transistor 148 is switched to be conductive and does not permit re-charging of the capacitor 142 until after the set pulse of the monostable circuit 150 has elapsed. If more precise delays in the switching on and/or pause are desired, then this switch 22 can also be realized digitally, with a defined pulse generator and counters as well as digital comparators.

Figure 11:
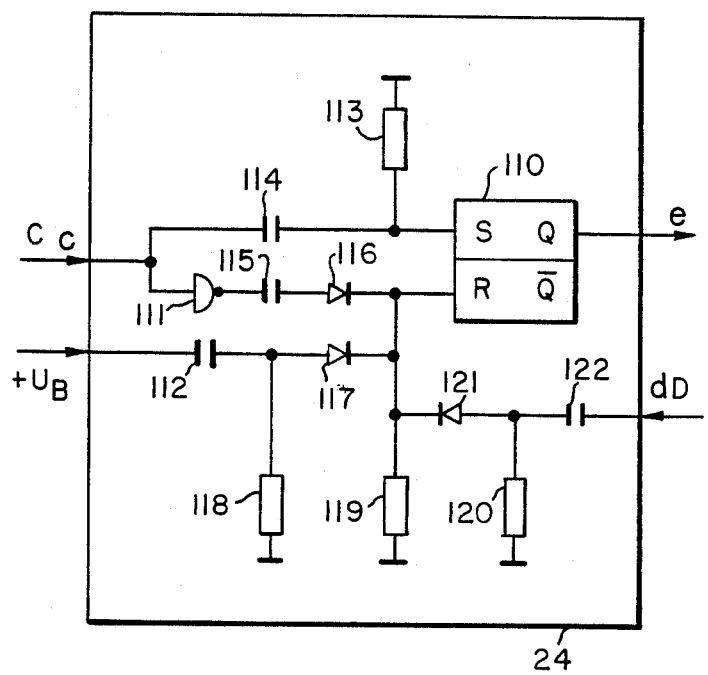
FIG. 11 shows an exemplary embodiment of a switching logic.

An exemplary embodiment of the switching logic 24 will now be described in further detail in conjunction with FIG. 11.

The switching logic 24 is intended to coordinate the switching ON and OFF of the high frequency oscillator 1 in such a way that only defined switching states are possible. By switching the operating voltage $+U_B$ of the apparatus ON, a bistable circuit 110, for example an RS flip-flop, is set at the reset input R in such a way that the output signal e assumes a logical LOW level. If the apparatus is switched ON by means of the manual switch 21 and/or by means of the automatic switch 22, then the signal c is switched via the line C to a logical HIGH level, as a result of which the bistable circuit 110 is set via the input S such that the signal e assumes the level of logical HIGH. This state is maintained by the bistable circuit 110 until such time as either the signal d via the line D switches to the HIGH level or the signal c switches to the LOW level. The signal d comes from the automatic shutoff devices 25, 26 or 27 and is carried via the capacitor 122 directly to the input R of the bistable circuit. The signal c comes from the switching 21 and/or 22 and before it is carried to the input R of the bistable circuit 110 it must be inverted in an inverter element 111.

The dynamic triggering of the bistable circuit via the capacitors 112, 114, 115 and 122 prevents the immediate restarting of the high frequency generator after its automatic shutoff by the automatic shutoff devices 26, 26 or 27 whenever the signal c continues at a HIGH level. After each automatic shutoff of the high frequency generator, the switch 21 and/or 22 must be reactivated in this manner.

Figure 12:
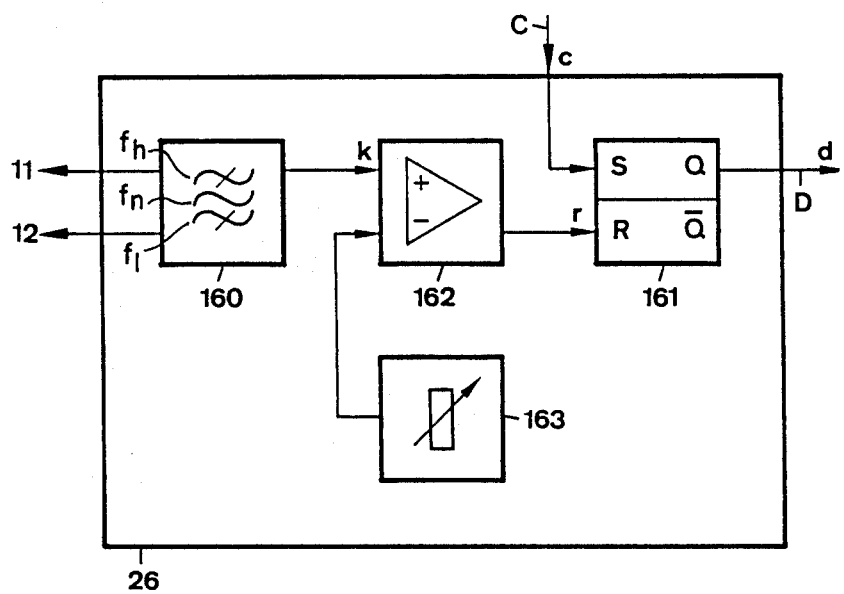
FIG. 12 shows an exemplary embodiment of an electrical arc monitor.

An exemplary embodiment of an electric arc monitor 26 will now be described, referring to the schematic diagrams in FIGS. 12 and 13.

As already described above in conjunction with FIG. 1, electric arcs occur from a specific stage in the coagulation process on, namely whenever an electrically insulating film is formed within which, at sufficiently high voltage $U_{HF}$, an electrical field intensity high enough to ignite electric arcs is formed, the formation of this film being the result of coagulation and/or dessication or drying out of the biologic tissues and/or vapor formation in the boundary region between the contact face of the coagulation electrode and the biologic tissues. It is known that electric arcs are nonlinear electrical resistances as a result of which the electric current is not proportional to the electric voltage. It is also known that because of the nonlinear property of the electric arcs, alternating current which flows through electric arcs is distored as compared with the driving voltage in such a way as to produce harmonic frequencies of the frequency of the alternating voltage. What is novel is the recognition that because of the stochastic properties of the electric arcs between the coagulation electrode and the biologic tissues, anharmonic frequencies of the frequency of the driving voltage are produced as well.

As long as no electric arc is present between the coagulation electrode 13, 15 and the tissue, only the base frequency $f_1$ and, more or less intensively, the integral harmonic frequencies $f_h$ of the basic frequency are present at the output of the high frequency generator 11, 12. The zero order harmonic frequency $f_o$ is not present here.

However, as soon as electric arcs do ignite between the coagulation electrode 13 or 15 and the tissue of the patient 17, the arc is produced because of the nonlinear behavior of the electrical resistance, and because of the stochastic frequency of the arc per unit of time, anharmonic frequencies $f_n$ between the harmonic frequencies $f_h$ are also produced.

In accordance with the invention, the generation of anharmonic frequencies $f_n$ of the base frequency $f_1$ of the high frequency oscillator 1 during each coagulation process is used as a criterion for the automatic shutoff of the current $I_{HF}$. The arc monitor 26 is therefore equipped with a filter 160, which selectively passes a specific anharmonic frequency $f_n$ or a more or less wide frequency spectrum between two adjacent harmonic frequencies $f_h$ or a plurality of more or less wide frequency spectra of the anharmonic frequencies $f_n$ between various adjacent harmonic frequencies $f_h$ of the base frequency $f_1$ of the high frequency oscillator 1 and damps both the base frequency $f_1$ and the relevant harmonic frequencies $f_h$ of the high frequency oscillator 1 sufficiently.

The output signal k of the filter 160 is supplied to a voltage comparator 162, the output signal r of which acts upon a bistable circuit 161 such that the bistable circuit furnishes a shutoff signal d to the line D, causing the current $I_{HF}$ to be shut off until, by renewed switching on via manual 21 and/or automatic 22 switches, a switch-on signal c via a line C again acts upon the bistable circuit 161 such that the current $I_{HF}$ is switched back on again. The threshold voltage of the voltage comparator 162 can be set at a voltage source 163.

The filter 160 can be assembled by various technologies. One suitable means is a ceramic filter, which passes one or more of the anharmonic frequencies $f_n$ below the base frequency $f_1$ of the high frequency oscillator and damps both the base frequency $f_1$ and its harmonics, including the frequency 0. Ceramic filters have the advantage that they can be produced relatively economically, that they afford sufficient electrical insulation between the filter input and the filter output, and that a plurality of such filters, which are turned to various discrete anharmonic frequencies and/or frequency bands between two adjacent harmonic frequencies, can economically be connected in parallel, which increases the redundancy of the arc monitor.

Figure 13:
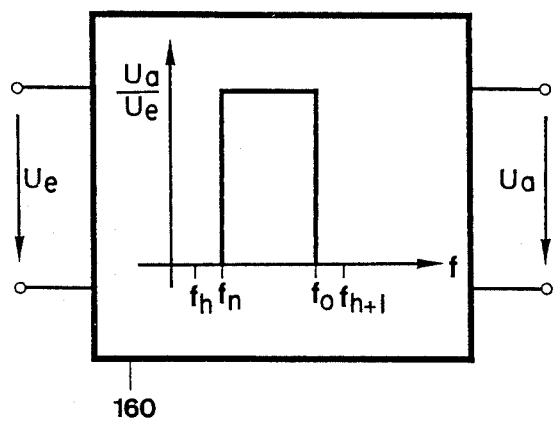
FIG. 13 is a diagram of a filter characteristic of the filter 160.

In FIG. 13, an idealized filter characteristic of a filter 160 suitable for the arc monitor 26 is shown. $U_e$ stands for the input voltage and $U_a$ stands for the output voltage of the filter. The frequency $f_h$ is a relevant harmonic frequency of the base frequency $f_1$, including this base frequency itself. Only the harmonic frequencies that are present in the frequency spectrum of the high frequency generator are relevant. The frequency $f_h$ is an arbitrary harmonic frequency, and $f_{h+1}$ stands for the next higher relevant harmonic frequency. Both the lower threshold frequency $f_u$ and the upper threshold frequency fof the filter 160 must be dimensioned such that sufficient intervals from the harmonic frequencies $f_h$ and $f_{h+1}$ are present, so that tolerances of the frequency $f_1$ and thus of its harmonics are taken into account.

Figure 14:
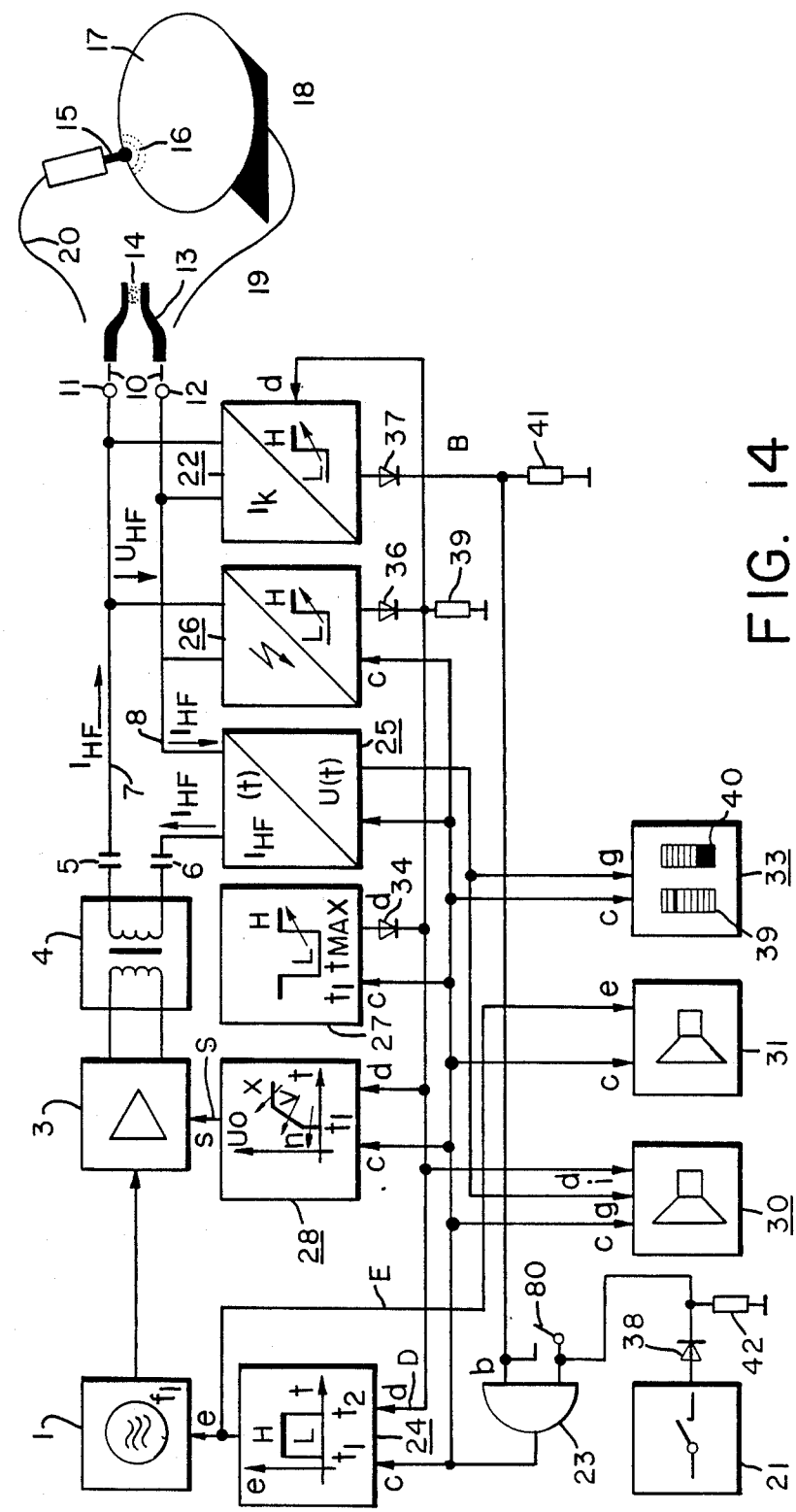
FIG. 14 is a block circuit diagram of an exemplary embodiment of the apparatus according to the invention for thermal coagulation of biological tissue by means of high frequency current.

An exemplary embodiment of an apparatus for thermal coagulation of biologic tissues by means of high frequency electrical alternating current, which attains the object of the invention in a different manner from the exemplary embodiment described in conjunction with FIGS. 4 and 5, will now be described in conjunction with FIG. 14. In this version, the shutoff of the current $I_{HF}$ is effected primarily by means of the arc monitor 26, which is described in further detail in conjunction with FIGS. 12 and 13. In this version, the current monitor 25 serves solely to convert the amplitude of the current $I_{HF}(t)$ into a voltage U(t) proportional to this current, for which the elements 50, 51, 52, 53, 55, 58, 59, 60 and 62 in the arrangement shown in FIG. 2 can for instance be used. All the other advantageous improvements in this exemplary embodiment are identical to the improvements of the version shown in FIG. 4 that are described and shown in FIGS. 5–11.

We claim:

1. High frequency electro surgical apparatus for thermal coagulation of biologic tissues comprising a high frequency electric generator having a fundamental frequency ($f_1$) of operation and having an output circuit equipped with a coagulation electrode for contact with biological tissues of a patient and with switching means for manual or automatic activation of said generator to produce an output of high frequency current and for automatic switching off of a coagulation operation in dependence upon changes in electric conductivity of said tissues of said patient, and further comprising, in accordance with the invention:

electrical monitoring means (25) having an input coupled to said output circuit of said high frequency generator for monitoring amplitude fluctuations of the output of said high frequency electric generator during each coagulation operation by monitoring at least one of the current and voltage of said output, said monitoring means including means (50, 51, 52) for deriving from the output high frequency current ($I_{HF}$) of said generator, a voltage proportional to the amplitude fluctuations (A(t)2) of said high frequency current ($I_{HF}$), first detection means (53, 55, 58, 60, 62) coupled for being responsive to the output of said voltage deriving means for producing, at an output of said first detection means, a first DC voltage ($U_a$) proportional to said amplitude fluctuations (A(t)) of said high frequency current ($I_{HF}$) and second detection means (54, 56, 61, 63) coupled for response to rising portions of fluctuations of said high frequency current and constituted as a peak value detector, for producing, at an output of said second detection means, a second DC voltage ($U_b$) which rises proportionally to the rising portion of fluctuations of said high frequency current;

voltage comparison means (67) coupled for response to said respective outputs of said first and second detection means for comparing said first DC voltage ($U_a$) and a predetermined adjustable fraction ($kU_b$) of said second DC voltage and producing a comparison result signal at an output of said comparison means;

a bistable switching control circuit (70) coupled to said output of said comparison means and connected for being set by the comparison result signal of said voltage comparison means (67) when said first DC voltage ($U_a$) becomes smaller than said predetermined fraction ($kU_b$) of said second DC voltage and thereby to produce an output control signal (Q);

means coupled for response to said bistable circuit (70) and connected to said high frequency generator for shutting off the output of said high frequency generator in response to said output control signal (Q) of said bistable circuit (70), and means (23) for reactivating, and usable for initially activating, the output of said high frequency generator in response to operation of a manual switch (21), to operation of an automatic switch (22) or to both said manual switch and said automatic switch.

2. Apparatus according to claim 1, further comprising:

means (26) coupled to said output circuit (11, 12) of said high frequency generator for monitoring the occurrence of anharmonic frequencies relative to the fundamental frequency ($f_1$) of said high frequency electric generator, including a filter (160) for passing at least one said anharmonic frequency resulting from formation of an electric arc between said coagulation electrode (15;13) and biological tissues of a patient and for simultaneously damping both said fundamental frequency ($f_1$) and its harmonics, second voltage comparison means (162) for comparing the output of said filter (160) with a predetermined voltage value and providing a comparison signal (r) at an output of said second voltage comparison means and a second bistable circuit (161) coupled for response to the output of said second comparison means and connected for being set in response to said comparison signal (r) of said second voltage comparison means (162) and providing an output signal (Q) at an output of said second bistable circuit (161);

means coupled for response to the output of said second bistable circuit for switching off the output of said high frequency generator in response to said output signal (Q) of said second bistable circuit (161) responsive to said comparison signal (r) of said second voltage comparison means.

3. Apparatus according to claim 2, further comprising an amplitude modulator (2) for and within said high frequency generator, a switch-on time limiter (27) and control unit (28) coupled at least for response to said reactivating means (23) and for affecting said amplitude modulator (2) for causing the no load voltage ($U_o$) of said high frequency generator to rise from the instant ($t_1$) of each switching on of the high frequency generator, beginning at an adjustable minimum voltage level ($U_{min}$) at an adjustable speed (v) until the high frequency generator is switched off either manually or automatically by said second bistable circuit (161) or by said switch-on time limiter (27); and further equipped with means connected to said amplitude modulator for adjusting the maximum voltage level ($U_{max}$) of said high frequency generator at which said high frequency generator is maintained from the time said maximum level is reached until said high frequency generator is switched off, and means coupled to affect said amplitude modulator and to respond to the outputs of said bistable circuits for bringing the output voltage of said high frequency generator in said output circuit thereof to the level zero at the same time as said high frequency generator is switched off.

4. Apparatus according to claim 3, wherein said control unit (28) includes a digital/analog converter (83), a programmable counter (82), a pulse generator (86) of adjustable pulse frequency (v), a digital comparator (84) and first and second digital preselection switches (81, 85), connected together so that said digital-to-analog converter (83) produces an analog control signal (S), the level of which is determined by said programmable counter (82), with the minimum count level (n) being adjustable by said first digital preselection switch (81) and is taken over into said programmable counter (82) at the instant ($t_1$) of switching on of said high frequency generator and so that when said high frequency generator is switched on, the pulse generator (86) is started at the instant of switching on of said high frequency generator and supplies pulses to said programmable counter (82) for incrementing the counter content corresponding to said minimum count level (n) set by said first preselector switch (81), and so that at the output of said counter (82), addition to delivering its output to said digital-to-analog converter, supplies its output to said digital comparator (84) for comparison with a digital value set in said second digital preselector switch (85) corresponding to a maximum level (x) and when equivalence is found in said comparison, houses said pulse generator (86) to stop so that thereafter said control signal (S) provided by said digital-to-analog capacitor remains steady, said control unit (28) having a stop signal output for resetting said counter (82) through its reset input (RS) and thereby setting said control signal (S) to zero value as soon as a switch off signal (d) is present.

5. Apparatus according to claim 2, further comprising a second coagulation electrode, one of said coagulation electrodes being monopolar and the other of said coagulation electrodes being bipolar, said electrodes not being simultaneously connectable to or usable in said output circuit of said high frequency generator, but being interchangeably available for different applications, and also comprising a neutral electrode (18) for use with said monopolar electrode, an automatic switching means for immediately, or after an adjustable and retriggerable delay period, switching on said high frequency generator when said monopolar coagulation electrode (15) and said neutral electrode (18) simultaneously touch, in an electrically conducting manner, tissue of a patient or when both poles of said bipolar coagulation electrode (13) simultaneously touch, in an electrically conducting manner, tissue of a patient, said automatic switching means containing a monostable circuit (150) of adjustable pulse duration arranged to be triggered by a switch off signal (d) for providing a switch-on of said high frequency generator only after said pulse duration of said monostable circuit (150) has terminated.

6. Apparatus according to claim 2 further comprising a current indicator (33) coupled for response to said output circuit of said high frequency generator and having a first display instrument (125) for displaying the value of current output ($I_{HF}$) of said high frequency generator and a second display instrument (124) for displaying the peak value of said high frequency current output ($I_{HF}$) of said high frequency generator during each coagulation operation, including means for continuing the display of said peak value after switching off of said high frequency generator until the instant in which said high frequency generator is turned on again, and discharge circuit means (122, 123, 124) for discharging said means for continuing said peak value display (127) to allow said second display instrument (124) and said peak value displaying continuing means (127) to take on at once the new peak value at said instrument in which said high frequency generator is turned on.

7. Apparatus according to claim 2 further comprising an accoustic signal generator (30) coupled for response to the outputs of said bistable circuits and to said electrical monitoring means (25) for generating audible tones in accordance with different stages of a coagulation operation, said tones including a fundamental tone having a frequency ($f_o$) when said high frequency generator is switched on while no output current therefrom yet flows and having a frequency which rises or falls proportionately to intensity of the output current of said high frequency generator, and a staccato tone of high sound frequency which is produced during a following interval after said high frequency generator is switched off.

8. Apparatus according to claim 2 comprising also an accoustic signal generator (31) coupled for response to a switching input (e) of said high frequency generator, to said reactivation means (23) and to the outputs of said bistable circuits (70, 161), for providing a warning signal when said high frequency generator is switched on while no manual or automatic switch for said high frequency generator is switched on or when said high frequency generator is switched off while at least one switch for switching on said high frequency generator is switched on, said accoustic signal generator (31) having connected therewith a monostable circuit (44) for delaying the operation of said accoustic signal generator with respect to every switching on of said high frequency generator.

9. Apparatus according to claim 2 wherein said reactivating means for the output of said high frequency generator comprises and AND gate (23) having two inputs, an automatically timed switching device (22) having an input coupled for response to said output circuit of said high frequency generator and an output and containing a timing circuit for producing an output signal a manual switching device, and said AND gate having its inputs connected to said output of said timed switching device and to said manual switching device (21) and an output connected for controlling the switching on again of said high frequency generator, whereby said high frequency generator can be turned on only when both said timed switching device (22) and said manual switching device (21) are in the switched on position.

10. Apparatus according to claim 2 containing also a switch-on interval limiter (27) having an input connected to the output of said reactivating means and an output connected to a control connection (d) to which the respective outputs of said bistable circuits (70, 161) are connected, for automatic switching off of said high frequency generator after a preset interval, said limiter being connected so that the maximum switched-on time thereby set begins with triggering by a switch-on signal (C) from said reactivating means.

* * * * *